United States Patent
Maruo et al.

[11] Patent Number: 5,932,480
[45] Date of Patent: Aug. 3, 1999

[54] MEASUREMENT METHOD AND KIT FOR HEMOGLOBIN A1C

[75] Inventors: Naoko Maruo, Yokohama; Masuo Inoue, Kawasaki, both of Japan

[73] Assignee: Tosoh Corporation, Yamaguchi-Ken, Japan

[21] Appl. No.: 08/816,326

[22] Filed: Mar. 13, 1997

[30] Foreign Application Priority Data

Mar. 14, 1996 [JP] Japan .................................. 8-057932
Jan. 30, 1997 [JP] Japan .................................. 9-016340

[51] Int. Cl.⁶ .................................................. G01N 33/72
[52] U.S. Cl. ............................ 436/66; 436/67; 436/808; 436/518; 436/524; 436/538; 435/7.1; 435/7.9; 435/7.92; 435/810; 435/960; 435/975
[58] Field of Search ............................... 422/61; 436/501, 436/518, 524, 527, 533, 534, 536, 538, 540, 63, 66, 67, 174, 175, 808, 823, 824, 826; 435/2, 7.1, 7.72, 7.8, 7.9, 7.92, 810, 960, 961, 975

[56] References Cited

U.S. PATENT DOCUMENTS

| | | | |
|---|---|---|---|
| 4,247,533 | 1/1981 | Cerami et al. | 422/61 X |
| 4,629,692 | 12/1986 | Dean | 435/7.7 |
| 4,647,654 | 3/1987 | Knowles et al. | 530/326 |
| 4,658,022 | 4/1987 | Knowles et al. | 530/402 |
| 4,727,036 | 2/1988 | Knowles et al. | 530/387.9 |
| 4,847,209 | 7/1989 | Lewis et al. | 436/533 |
| 5,206,144 | 4/1993 | Zeuthen et al. | 435/7.25 |
| 5,470,759 | 11/1995 | Sugiyama et al. | 436/541 |
| 5,484,735 | 1/1996 | Davis et al. | 436/548 |
| 5,506,114 | 4/1996 | Sangha | 435/15 |
| 5,541,117 | 7/1996 | Karl et al. | 436/518 |

FOREIGN PATENT DOCUMENTS

| | | |
|---|---|---|
| 5249110 | 9/1993 | Japan . |
| 06167495 | 6/1994 | Japan . |

*Primary Examiner*—Maureen M. Wallenhorst
*Attorney, Agent, or Firm*—Sughrue, Mion, Zinn, Macpeak & Seas, PLLC

[57] ABSTRACT

A sample containing hemoglobin A1c (HbA1c) is simultaneously brought in contact with a solid phase and anti-HbA1c antibody, the anti-HbA1c antibody bound to the adsorbed HbA1c on the solid phase and the anti-HbA1c antibody in solution are separated, and the anti-HbA1c antibody bound to the adsorbed HbA1c on the solid phase is detected. HbA1c % is determined by one-step immunoassay, and the time required for measurement is shortened in comparison with conventional immunoassay methods. Since the exposure time to the pretreatment solution present in the reaction solution during the immune reaction is shortened, formation of a precipitate in the sample as well as inactivation of the enzyme of the enzyme-labeled anti-HbA1c antibody, when used, is reduced.

6 Claims, 2 Drawing Sheets

MEASUREMENT METHOD AND KIT FOR HEMOGLOBIN A1C

BACKGROUND OF INVENTION

1. Field of Invention

The present invention relates to a one-step immunoassay method and immunoassay kit for measuring percentage of hemoglobin A1c in a sample.

2. Related Art

Hemoglobin A1c (HbA1c) is a glycated hemoglobin formed by binding between the amino group of the N-terminal valine of the β-chain of hemoglobin and glucose aldehyde group resulting first in a Schiff's base and further a stable ketoamine by Amadori Rearrangement. Since percentage of HbA1c reflects mean blood sugar content prior to 1 to 2 months, it is well accepted for blood sugar level management.

So far, an instrument performing measurement by high performance liquid chromatography (HPLC) using ion exchange chromatography, namely a glycohemoglobin analyzer, has been primarily used for the measurement of HbA1c % in blood. Although this method gives excellent producibility, it has also been pointed out that several disadvantages exist, including requirement of a specialized HPLC analyzer system, limitations of processing capability, and inaccurate results with other forms of hemoglobin. In addition, it requires highly technical maintenance.

In recent years, HbA1c measurement techniques other than the HPLC method have been developed to solve the above mentioned problems, and such reagents have been marketed. Immunoassay in particular has been applied for the measurement of HbA1c % due to its high specificity.

Sandwich assay, for example, using two antibodies, has been considered for use as an immunoassay for HbA1c. On the other hand, adsorption-immunoassay, wherein hemoglobins including HbA1c in a sample are physically adsorbed to a solid phase and the adsorbed HbA1c is detected with an antibody having high specificity for HbA1c, is well known. In this method hemoglobins are directly adsorbed to a solid phase, and adsorbed HbA1c is considered to be in a proportion equal to the proportion in hemoglobins when excess hemoglobins are applied to the limited surface of the solid phase. Since HbA1c is expressed in the clinical field as a percentage (%) relative to the total amount of hemoglobins, the percentage of HbA1c in the blood can be determined without measuring the absolute amount of HbA1c nor of total hemoglobins, when the percentage of HbA1c in the adsorbed hemoglobins on a solid phase is in a proportion equal to that in blood. In this method it is required for hemoglobins to be adequately adsorbed on the solid phase. Sequential steps are, therefore, carried out in this method. Namely, hemoglobins are first adsorbed on the surface of a solid phase such as latex particles or polystryrene beads, the resulted solid phase is then washed or separated to remove unadsorbed materials as necessary, and the HbA1c adsorbed on the solid phase is specifically detected by an anti-HbA1c antibody that specifically binds HbA1c. Enzyme immunoassay (EIA) reagents using this method are also commercially available.

In this two-step assay using a commercially available EIA kit, since a washing procedure is required between the first adsorption step and the second immunoreaction step, the procedure is more complex and requires longer processing times as compared with a simultaneous or one step immunoassay. In addition, there is also a possibility of the hemoglobin adsorbed onto the solid phase being released during the washing steps. Moreover, in these types of kits, since the glycated N-terminal residue of the hemoglobin β-chain is used for the reaction with specific antibody to HbA1c, there are many situations which require strong denaturing conditions to expose the glycated N-terminal residues during or prior to adsorption on the solid phase. However, since there is a high possibility that the enzyme antibody conjugate may be inactivated under these conditions, a simultaneous adsorption-immune reaction step may not be applied due to possible inactivation of enzyme and/or antibody of enzyme labeled anti-HbA1c antibody. Due to the strong denaturing conditions used in such commercially available kits, a denatured blood sample must be used immediately after its preparation, because variation in the measured values occurs due to the formation of precipitates and so forth, thus preventing the obtaining of correct values. Consequently, this method is not considered to be suitable for processing large numbers of samples.

On the other hand, immunoassay has also been applied to latex agglutination instead of EIA. A hemolyzed specimen is added to an unsensitized latex suspension to adsorb the hemoglobins on the surface of latex, then the mouse monoclonal antibody specific to HbA1c is added followed by the addition of anti-mouse IgG polyclonal antibody for the resulting agglutination wherein the degree of agglutination reflects HbA1c (%) in a sample. Although this method does not require a washing step, since a large amount of latex is required to adsorb hemoglobins, there is a possibility of the occurrence of non-specific agglutination of latex resulting in the appearance of abnormally high values or the risk of difficulty in detecting increased agglutination caused by antibody-antigen reaction of HbA1c.

Diabetes and other adult related diseases are steadily increasing with increase in the elderly population. Accompanying this trend, since diagnostic parameters such as HbA1c % which is widely recognized as an indicator of blood sugar status is the object of diagnosis when examinations are required to be performed on elderly persons, it is necessary to improve specimen processing capacity. There is therefore a tremendous need for the development of diagnostic reagents that enable processing to be performed easily, accurately and in large volume. The currently available HPLC method has a low specimen processing capacity and specialized instrumentation requirement with complexity in maintenance. On the other hand, the currently available EIA and latex agglutination methods require complex procedures and give inaccurate results, for example, because of the several reasons mentioned above.

As the result of conducting studies on developing a method enabling measurement of HbA1c % in a sample easily and accurately on the basis of immunoassay with high specificity, the inventors of the present invention constructed a method that allows measurement of HbA1c % in a sample using a one-step procedure in which adsorption of hemoglobins on the solid phase and reacting of antigen HbA1c and anti-HbA1c antibody are performed simultaneously, thereby leading to completion of the present invention.

Namely, the present invention discloses a method for measuring HbA1c % comprising the steps of simultaneously bringing a sample containing HbA1c in contact with a solid phase and an anti-hemoglobin A1c antibody resulting in the formation of adsorbed HbA1c bound to an antibody, separating the bound anti-hemoglobin A1c antibody to the solid phase from unbound materials, and detecting the amount of bound anti-hemoglobin A1c antibody or the unbound anti-hemoglobin A1c antibody.

In addition, the present invention discloses a one-step immunoassay kit for measuring hemoglobin A1c % in a sample comprising a solid phase and an anti-hemoglobin A1c antibody.

DETAILED DESCRIPTION

Figure 1:
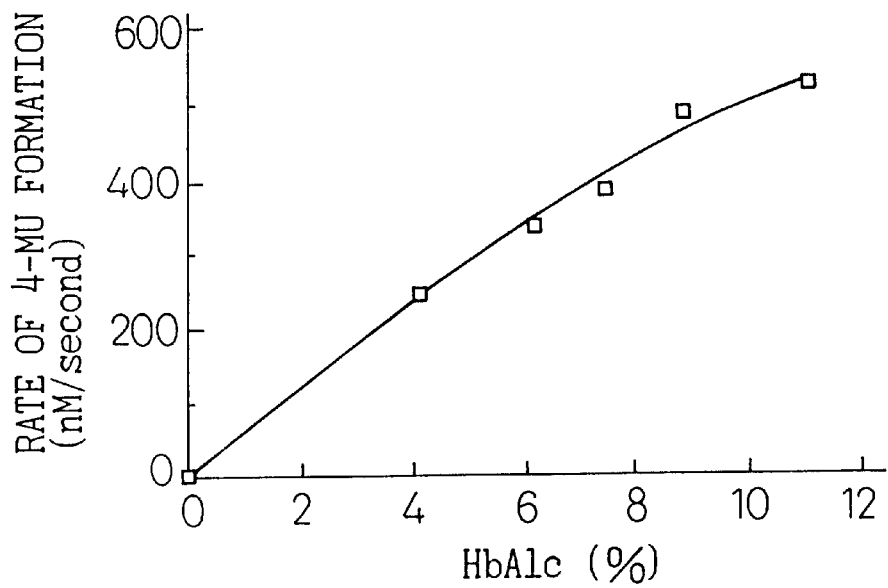
FIG. 1 is a standard curve for the measurement of HbA1c % using the one step 40-minute incubation reaction employed in Example 1.

In the present invention, it is necessary to hemolyze blood samples prior to measuring HbA1c % in the blood. There is no particular limitation on the method for hemolyzing the blood, and various methods can be used, examples of which include the use of a hypotonic liquid such as water, or a surfactant.

After hemolysis, pretreatment of the sample is performed. HbA1c is denatured and unstable HbA1c can be removed by this pretreatment. There is no particular limitation required for the pretreatment step, and various methods can be employed. For example, KSCN or other chemicals can be applied. However, in order to minimize detrimental effects on the immunoassay method in the next step, namely to reduce precipitates formation of the sample caused by pretreatment solution still present in the reaction mixture, and to reduce inactivation of enzyme and/or antibody in the case of using enzyme-labeled antibody, it is preferable to use mild conditions and lesser amounts in pretreatment. Thus, it is preferable that pretreatment be performed under, for example, mildly acidic conditions. Mildly acidic conditions refer to a pH of preferably 3.0 to 6.9 and more preferably 4.0 to 6.0. Examples of buffers used for pretreatment under these conditions include aliphatic carboxylate buffers or borate buffers. Examples of aliphatic carboxylate buffers include monocarboxylate and dicarboxylate buffers, and more specifically, succinate, malonate, fumarate, maleate, glutarate or acetate buffers. Succinate, glutarate or acetate buffers are preferable, while succinate buffer is particularly preferable.

Pretreatment under mildly acidic conditions enables HbA1c to be denatured while preserving the $\alpha 2\beta 2$ structure of hemoglobin, and unstable HbA1c to be removed. Furthermore, hemolysis and pretreatment may be performed sequentially or simultaneously.

Thus, once the sample is hemolyzed and pretreated, a solid phase and an anti-HbA1c antibody are simultaneously brought in contact. There is no particular limitation for the solid phase used in this method capable of adsorbing hemoglobins, and examples of the solid phase include tubes, beads, plates, microparticles or filter paper made of materials such as glass, polystyrene, latex and paper. Regardless of the solid phase used, a larger surface is preferable since it results in an increased amount of adsorbed hemoglobins and improved measurement sensitivity.

On the other hand, there is also no particular limitation on the anti-HbA1c antibody used in the reaction provided it specifically recognizes HbA1c. Monoclonal or polyclonal antibody as well as their fragments may be used. It is preferable that this anti-HbA1c antibody be labeled to facilitate detection following the immune reaction. There is no particular limitation on this label provided it is normally used in detection of immune reactions, example of which includes enzymes, radioisotopes and fluorescent materials, with enzyme labeling being particularly preferable. More specifically, examples of enzymes include alkaline phosphatase, peroxidase and $\beta$-D-galactosidase, examples of radioisotopes include $^{125}$I, and examples of fluorescent materials include fluorescein. In addition, in the case where the anti-HbA1c antibody is not labeled, another antibody (2nd antibody) that recognizes anti-HbA1c antibody should be labeled, reacted and used for detection. The same labels are used in this case as those described above. Furthermore, it is preferable that an adequate amount of anti-HbA1c antibody be added for binding with the HbA1c adsorbed on the solid phase.

An analyte HbA1c in a sample in the present invention is reacted simultaneously by bringing the sample into contact with a solid phase and anti-HbA1c antibody. The adsorption of the HbA1c onto the solid phase and the reaction of the HbA1c with anti-HbA1c antibody is characterized by being performed in a single incubation step. Examples of methods for accomplishing this include a method wherein solid phase and anti-HbA1c antibody are simultaneously added to the sample, and a method wherein solid phase and anti-HbA1c antibody are mixed in advance followed by the addition of sample. There is no particular limitation on the conditions for the adsorption of the HbA1c in the sample with the solid phase and the reaction with anti-HbA1c antibody, and the conditions for ordinary immunoassay reactions can be employed. However, the reaction time should be as short as possible provided it does not hinder detection. The reaction time is normally 5 to 60 minutes, preferably 5 to 50 minutes and more preferably 5 to 15 minutes. Not only is this done to improve measurement efficiency, but also to reduce the formation of precipitates in the sample caused by the pretreatment solution still present in the reaction mixture. In addition, in the case of using an enzyme-labeled anti-HbA1c antibody, the short time incubation is also done to reduce inactivation of enzyme and/or antibody by the pretreatment solution. Furthermore, in the case of the anti-HbA1c antibody which is not labeled, it is preferable to add a labeled 2nd antibody and allow that antibody to react.

After adsorption of the HbA1c on the solid phase and reaction with anti-HbA1c antibody, the anti-HbA1c antibody bound to the HbA1c which has been adsorbed on the solid phase and unbound materials are separated and the resulted solid phase is washed as necessary. Next, anti-HbA1c antibody bound to the HbA1c adsorbed on the solid phase, or the anti-HbA1c antibody in solution, is detected to determine the HbA1c % in the sample. At this time, in the case where the anti-HbA1c antibody is labeled, detection should be performed using the label on the anti-HbA1c antibody. In addition, in the case where the anti-HbA1c antibody is not labeled, the label of a 2nd antibody should be detected. A method suitable for detecting the label can be suitably used for detection thereof.

In carrying out the measurement of the present invention, it is preferable that the materials used in the immunoassay be provided in the form of a kit. This kit comprises a solid phase and anti-HbA1c antibody, and is used to perform the one-step immunoassay for the measurement of HbA1c %.

The present invention enables HbA1c % to be measured in a one-step immunoassay. As a result, the time required for measurement can be reduced in comparison with measurement of HbA1c in two steps as in conventional immunoassay methods. The amount of time the sample is in contact with the pretreatment solution still present in the reaction mixture is shortened thereby preventing the formation of precipitates in the sample. In addition, in the case where an enzyme-labeled anti-HbA1c antibody is used in a one-step immunoassay, inactivation of the enzyme and/or antibody caused by the presence of pretreatment solution can also be reduced when a shorter incubation time is applied. Moreover, since only one step is required for separation of bound anti-HbA1c antibody and unbound materials in solution, there is a lesser risk of hemoglobin releasing from the solid phase.

Moreover, the present invention enables the most recent HbA1c % measurement values to be available before an interview with a patient by drawing blood from the patient and measuring HbA1c %. In addition, even if blood is drawn during the interview, results can be obtained without having the patient wait for so long due to the shorter incubation time required by the present method.

If the present method is used in combination with a commercially available automated immunoassay system, results can be obtained completely automatically with the exception of the initial hemolysation and pretreatment. In addition, since there is no need for a washing procedure during the course of the immune reaction, measurement time can be shortened thereby enabling a dramatic improvement in diagnostic usefulness.

Moreover, since measurement is possible with a commercially available fully automated immunoassay system, examination of other diabetes markers, such as insulin and C-peptide, can also be performed at the same time, thereby enabling a larger amount of information to be easily obtained at one time.

EXAMPLES

Example 1 Establishment of HbA1c Measurement Method and Preparation of Standard Curve Alkaline phosphatase-labeled anti-HbA1c antibody was prepared as described below. Namely, after bonding 2 mg of anti-HbA1c mouse monoclonal antibody (DAKO) with 2 mg of commercially available alkaline phosphatase derived from bovine small intestine (Biozyme) by S—S bonding, the resulting product was purified (see Ishikawa, E. ed., Enzyme Immunoassay Methods 3rd. Edition, Igaku Shoin, p. 117) by gel filtration (column: G3000SW, Tosoh; elution: 50 mM phosphate buffer (pH 7) containing 150 mM NaCl). The prepared alkaline phosphatase-labeled anti-HbA1c antibody was added to 0.1 M Tris buffer (pH 8.0) containing 5% bovine serum albumin, 10 mM $MgCl_2$, 0.1 mM $ZnCl_2$ and 0.1% $NaN_3$ to a concentration of 1.5 mA (1 mA is the concentration at which absorbance at 280 nm is 0.001). 100 μl of this reaction solution was poured into a cup followed by the addition of 12 polystryene beads (diameter: 1.4 to 1.6 mm)

The calibrators were prepared by separating the red blood cells from six patients which have different HbA1c % concentrations, washing the blood cells, hemolyzing them using purified water and finally by freeze-drying. After reconstituting with purified water, HbA1c % concentration of these calibrators was determined using a commercially available glycohemoglobin analyzer (HLC-723GHbIII, Tosoh). Reconstituted calibrator (20 μl) was added to 580 μl of 0.1 M succinate buffer (pH 5.0) containing 0.1% Triton X-100 and 0.1% $NaN_3$ followed by stirring and allowing to stand for 30 minutes at room temperature to prepare the sample solution for immunoassay.

The sample solution (10 μl) prepared above was added to the cup containing the above-mentioned labeled antibody and the beads, then immunoassay was performed in a single step using a commercially available, fully-automated immunoanalyzer (AIA-1200, Tosoh). Namely, after incubation for 40 minutes at 37° C., the beads, which adsorbed the antigen-antibody complex comprising enzyme-labeled anti-HbA1c antibody and antigen HbA1c, were washed followed by the addition of 220 μl of substrate solution (pH 10) containing 0.26 mg/ml of 4-methylumbelliferyl phosphate (4-MUP). The rate measurement of 4-methylumbelliferone (4-MU) formation was then performed at an excitation wavelength of 362 nm and an emission wavelength of 447 nm. Note that alkaline phosphatase converts 4-MUP to a fluorogenic substance, 4-MU.

The results are shown in FIG. 1. The HbA1c % concentration of the calibrators (as determined with a glycohemoglobin analyzer) are plotted on the horizontal axis, while the rate of 4-MU formation converted by labeled alkaline phosphatase is plotted on the vertical axis. The rate of 4-MU formation increased dependent on the concentration of HbA1c (%), thereby making it possible to prepare a standard curve.

Example 2 Correlation with Conventional Method using HPLC

After adding 20 μl of whole blood samples, obtained from normal adults and diabetes patients using EDTA as anticoagulant, to 580 μl of 0.1 M succinate buffer (pH 5.0) containing 0.1% Triton X-100 and 0.1% $NaN_3$ and stirring, the mixtures were allowed to stand at room temperature for 30 minutes to complete hemolyzation and pretreatment of samples. The solutions thus obtained were used as the sample solutions for immunoassay. The HbA1c concentration in a whole blood sample of a patient was determined in advance with a commercially available glycohemoglobin analyzer (HLC-723GHbIII, Tosoh) using the HPLC technique. One-step immunoassay measurement was performed on the AIA-1200 according to the method described in Example 1 to determine HbA1c % concentration.

Figure 2:
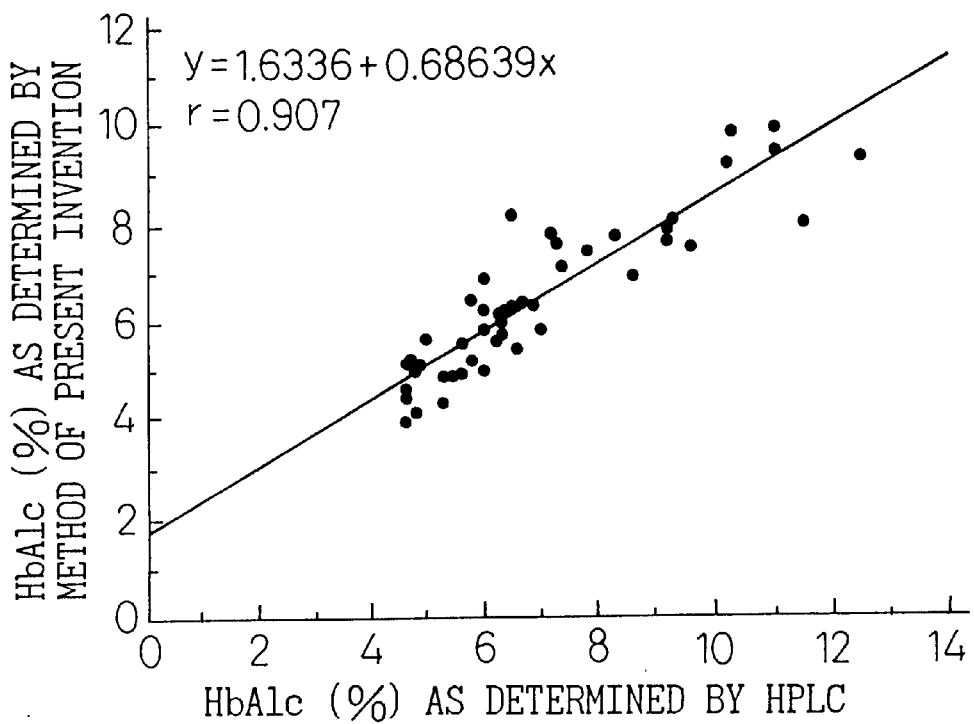
FIG. 2 is a correlation diagram between the one step 40-minute immunoassay method employed in Example 2 and a conventional HPLC method.

The results are shown in FIG. 2. FIG. 2 shows the measurement results for 50 diabetic samples. HbA1c concentrations (%) as determined using the HPLC method are plotted on the horizontal axis, while concentrations determined using the method of the present invention are plotted on the vertical axis. Good correlation was observed between the two methods, yielding a correlation equation of y=1.63+ 0.69x and a correlation coefficient of r=0.907, thus indicating a consistent trend of HbA1c % between the present method of invention and the conventional HPLC method.

Example 3 Intra-Assay and Inter-Assay Reproducibility

The intra-assay reproducibility of the one-step immunoassay method described above was evaluated using patient samples of four different concentrations of HbA1c. Those results are shown in Table 1.

TABLE 1

| HbA1c as determined by HPLC (%) | 4.50 | 6.10 | 8.20 | 10.00 |
|---|---|---|---|---|
| Measured values (%) | 3.81 | 5.66 | 7.01 | 7.44 |
| | 3.86 | 5.45 | 6.68 | 7.98 |
| | 4.02 | 5.21 | 6.58 | 7.82 |
| | 3.85 | 5.38 | 6.8 | 7.47 |
| | 3.86 | 5.2 | 6.86 | 7.7 |
| | 4.1 | 5.3 | 6.8 | 7.67 |
| | 3.94 | 5.27 | 6.94 | 7.98 |
| | 3.8 | 5.04 | 6.42 | 8.21 |
| | 4.15 | 4.83 | 6.98 | 8.33 |
| | 3.71 | 5.35 | | 7.96 |
| Mean | 3.91 | 5.27 | 6.79 | 7.86 |
| Standard deviation | 0.14 | 0.23 | 0.20 | 0.29 |
| Coefficient of variation CV (%) | 3.56 | 4.29 | 2.88 | 3.71 |

Intra-assay reproducibility was good, within a range of 3.5 to 4.3%, for all concentration ranges. In addition, when inter-assay reproducibility was studied using two concentrations of samples, favorable results were obtained of 4% or less as shown in Table 2.

TABLE 2

| HbA1c as determined by HPLC (%) | 4.8 | 10.3 |
|---|---|---|
| Measured values (%) | 4.88 | 8.28 |
| | 5.13 | 7.82 |
| | 5.00 | 8.44 |
| | 4.86 | 8.51 |
| | 4.95 | 8.33 |
| Mean | 4.96 | 8.28 |
| Standard deviation | 0.11 | 0.27 |
| Coefficient of variation CV (%) | 2.18 | 3.27 |

Example 4 Construction of a 10-Minute Assay System

Figure 3:
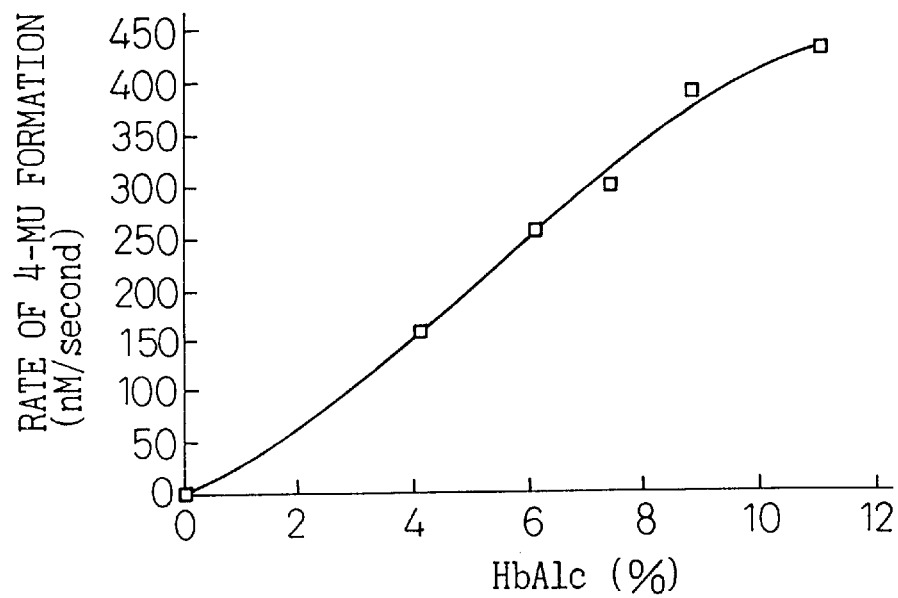
FIG. 3 is a standard curve for the measurement of HbA1c % using the one-step 10-method incubation reaction employed in Example 4.
Figure 4:
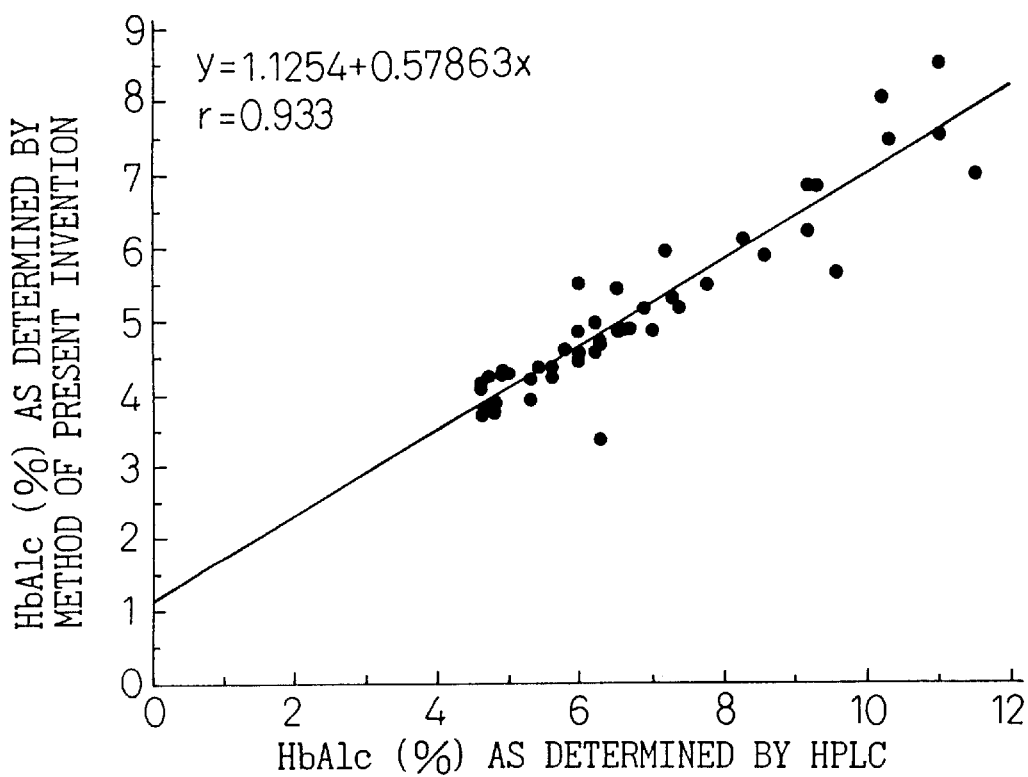
FIG. 4 is a correlation diagram between the one step immunoassay method employed in Example 4 in which the incubation time was shortened to 10 minutes and a conventional HPLC method.

Although the one-step immunoassay method of Examples 1 through 3 all need an incubation time of 40 minutes, a one-step immunoassay method was also constructed to reduce the incubation time to 10 minutes. Namely, immunoassay was performed using the alkaline phosphatase-labeled anti-HbA1c antibody solution of Example 1 increased to a concentration to 5 mA. The standard curve for this method is shown in FIG. 3. The concentration of the calibrators (as determined with a glycohemoglobin analyzer) are plotted on the horizontal axis, while the rate of 4-MU formation by labeled alkaline phosphatase is plotted on the vertical axis. In addition, the results of examining the correlation between a conventional HPLC method and this 10-minute assay system using the same patient samples as described in Example 2 are shown in FIG. 4. The measurement results are for 50 patient specimens. HbA1c % concentrations as determined with the conventional method (HLC-723GHbIII) are plotted on the horizontal axis, while the results determined according to the method of the present invention are plotted on the vertical axis. The correlation with the HPLC method was good, yielding a correlation equation of $y=0.579x+1.125$ and a correlation coefficient $r=0.933$.

In addition, the results of examining the intra-assay reproducibility in this 10-minute assay system in the same manner as the 40-minute measurement system shown in Example 3 are shown in Table 3, while the results of examining inter-assay reproducibility are shown in Table 4.

TABLE 3

| HbA1c as determined by HPLC (%) | 4.50 | 6.10 | 8.20 | 10.00 |
|---|---|---|---|---|
| Measured values (%) | 4.10 | 5.67 | 6.65 | 7.26 |
| | 4.43 | 5.54 | 6.52 | 7.27 |
| | 4.56 | 5.40 | 6.37 | 7.61 |
| | 4.65 | 5.60 | 7.05 | 7.61 |
| | 4.23 | 5.48 | 6.42 | 7.02 |
| | 4.51 | 5.98 | 6.5 | 7.31 |
| | 4.58 | 5.44 | 6.54 | 7.27 |
| | 4.26 | 5.25 | 6.52 | 7.25 |
| | 4.37 | 5.86 | 6.32 | 7.56 |
| | 4.49 | 5.50 | 6.61 | 7.13 |
| Mean | 4.42 | 5.57 | 6.55 | 7.33 |
| Standard deviation | 0.18 | 0.22 | 0.20 | 0.20 |
| Coefficient of variation CV (%) | 4.01 | 3.89 | 3.10 | 2.74 |

TABLE 4

| A1c as determined by HPLC (%) | 4.80 | 10.3 |
|---|---|---|
| Measured values (%) | 4.65 | 7.51 |
| | 4.83 | 7.64 |
| | 4.73 | 7.57 |
| | 4.64 | 7.63 |
| | 4.70 | 7.43 |
| Mean | 4.71 | 7.56 |
| Standard deviation | 0.08 | 0.09 |
| Coefficient of variation CV (%) | 1.62 | 1.16 |

Good results were obtained, demonstrating intra-assay reproducibility of 2.7 to 4.0% and inter-assay reproducibility of less than 4%. The correlation between the 40-minute system shown in Example 2 and the 10-minute assay system shown in the present Example was also good, exhibiting a correlation equation of $y=0.493+0.721x$ and $r=0.921$.

Example 5 Reactivity with Hemoglobin Variants

Measurement of glycated hemoglobin variants concentration was attempted using the method of the present invention described in Example 1 for six types of hemoglobin variants acquired (UBE2, HAMADEN, TAKAMATSU, CAPE TOWN, RIYADH and HIKARI; UBE2 and CAPE TOWN are α-chain variants, while the others are β-chain variants). Those results are shown in Table 5.

TABLE 5

| Name | Results as measured according to present invention (40 minute system) (A1c %) |
|---|---|
| UBE2 | 4.62 |
| HAMADEN | 2.13 |
| TAKAMATSU | 0 |
| CAPE TOWN | 0.22 |
| RIYADH | 0.42 |
| HIKARI | 0.78 |

These results show that hemoglobin variants are not recognized at all in the present method, thereby indicating that the present method is specific for normal HbA1c only, and that it is not affected at all by the presence of hemoglobin variants.

Example 6 Comparison of Pretreatment Solutions

After adding 580 μl of pretreatment solution A in 0.1 M succinate buffer (pH 5.03) containing 0.1% Triton X-100 and 0.1% NaN$_3$, or 580 μl of pretreatment solution B in distilled water (pH 7.15) containing 0.1% Triton X-100 and 0.1% $NaN_3$, to 20 µl of whole blood samples obtained from normal adults using EDTA as anticoagulant followed by stirring, the mixtures were allowed to stand for 30 minutes at room temperature to complete hemolyzation. These solutions were then used as the sample solutions for immunoassay. One-step immunoassay was then performed on the AIA-1200 in the same manner as in Example 4 to determine the concentrations of HbA1c. Those results are shown in Table 6.

TABLE 6

| Pretreatment solution | Rate of 4-MU formation | | |
|---|---|---|---|
| | 1st measurement | 2nd measurement | Mean |
| A | 134.441 | 148.458 | 141.450 |
| B | 3.949 | 4.355 | 4.152 |

As is clear from Table 6, performing pretreatment under weakly acidic condition results in obtaining a higher rate of 4-MU formation.

Furthermore, HbA1c concentration in the whole blood specimen was measured to be 5.4% with a glycohemoglobin analyzer (HLC-723GHbIII, Tosoh).

We claim:

1. A method for measurement of hemoglobin A1c comprising the steps of first pretreating a sample containing hemoglobin A1c to be measured under conditions which denature hemoglobin A1c, bringing the sample into simultaneous contact with a solid phase and an anti-hemoglobin A1c antibody resulting in immobilization of the hemoglobin A1c on the solid phase and binding of the anti-hemoglobin A1c antibody to the hemoglobin A1c to form immobilized anti-hemoglobin A1c antibody, separating the immobilized anti-hemoglobin A1c antibody from anti-hemoglobin A1c antibody in solution, and detecting the immobilized anti-hemoglobin A1c antibody or the anti-hemoglobin A1c antibody in solution as a measure of the hemoglobin A1c in the sample.

2. The method according to claim 1 wherein pretreating of said sample is performed under weakly acidic conditions.

3. The method according to claim 2 wherein pretreating is performed at a pH of 3.0 to 6.9.

4. The method according to claim 3 wherein an aliphatic carboxylate buffer or borate buffer is used for pretreating said sample.

5. The method according to claim 4 wherein said aliphatic carboxylate buffer is succinate, malonate, fumarate, maleate, glutarate or acetate buffer.

6. A kit for measurement of hemoglobin A1c comprising a pretreatment agent, which serves to denature hemoglobin A1c a solid phase and anti-hemoglobin A1c antibody useful for carrying out the method according to any one of claims 1 to 5.

* * * * *